US009982003B2

(12) United States Patent
Alliger et al.

(10) Patent No.: US 9,982,003 B2
(45) Date of Patent: May 29, 2018

(54) GROUP 3 METAL CATALYST SYSTEM AND PROCESS TO PRODUCE ETHYLENE POLYMERS THEREWITH

(71) Applicant: ExxonMobil Chemical Patents Inc., Baytown, TX (US)

(72) Inventors: Glen E. Alliger, Houston, TX (US); Roger A. Giovannangeli, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days. days.

(21) Appl. No.: 15/668,525

(22) Filed: Aug. 3, 2017

(65) Prior Publication Data

US 2018/0072766 A1   Mar. 15, 2018

Related U.S. Application Data

(60) Provisional application No. 62/393,464, filed on Sep. 12, 2016.

(51) Int. Cl.
| | |
|---|---|
| *C07F 17/00* | (2006.01) |
| *C07F 5/00* | (2006.01) |
| *C08F 4/6192* | (2006.01) |
| *C08F 4/6392* | (2006.01) |
| *C08F 236/04* | (2006.01) |
| *C08F 10/02* | (2006.01) |
| *C08F 36/00* | (2006.01) |

(52) U.S. Cl.
CPC ............... *C07F 17/00* (2013.01); *C07F 5/00* (2013.01); *C08F 10/02* (2013.01); *C08F 36/00* (2013.01)

(58) Field of Classification Search
CPC ........ C07F 5/00; C07F 17/00; C08F 4/61925; C08F 4/63925
USPC ................. 556/11; 526/114, 134; 534/11, 15
See application file for complete search history.

(56) References Cited

U.S. PATENT DOCUMENTS

| | | | | |
|---|---|---|---|---|
| 5,232,999 | A | * | 8/1993 | Conroy .................... C08F 4/54 502/152 |
| 6,288,191 | B1 | | 9/2001 | Nishiyama et al. |
| 8,962,744 | B2 | | 2/2015 | Horikawa et al. |
| 9,266,978 | B2 | | 2/2016 | Kaita et al. |
| 9,422,382 | B2 | | 8/2016 | Alliger et al. |
| 9,464,145 | B2 | | 10/2016 | Yang |
| 9,701,776 | B2 | | 7/2017 | Horikawa et al. |

FOREIGN PATENT DOCUMENTS

JP   48-56775 B   8/1973

OTHER PUBLICATIONS

Li et al., "Alternating and Random Copolymerization of Isoprene and Ethylene Catalyzed by Cationic Half-Sandwich Scandium Alkyls," Journal of American Chemical Society, 2009, vol. 131, No. 38, pp. 13870-13882.
Huang et al., "Synthesis, Characterization, and the Ethylene (co-)polymerization Behaviour of Half-titanocene Dichloride 2-aryliminoquinolin-8-olates," Catalysis Science Technology, 2012, 2, pp. 2090-2098.
Rodrigues et al., "Stereocontrolled styrene-isoprene copolymerization and styrene-ethylene-isoprene terpolymerization with a single-component allyl ansa-neodymocene catalyst," Polymer, 2008, vol. 49, No. 8, pp. 2039-2045.
Visseaux et al., "New Viscoelastic Materials Obtained by Insertion of an a-Olefin in a trans-Polyisoprene Chain with a Single-Component Organolanthanide Catalyst," Macromolecular Chemistry and Physics., 2001, vol. 202, No. 12, pp. 2485-2488.
Lee et al., "Copolymerizations of Olefins and Dienes with Homogeneous and Heterogeneous Catalysts," European Polymer Journal, 1997, vol. 33, No. 4, pp. 447-451.
Capacchione et al., Copolymerization of Ethylene with Isoprene Promoted by Titanium Complexes Containing a Tetradentate [OSSO]-Type Bis(phenolato) Ligand, Journal of Polymer Science Part A, 2010, vol. 48, No. 19, pp. 4200-4206.
Bonnet et al., "Copolymerization of Isoprene with Nonconjugated a,w-Dienes Using a Single component Samarocene Catalyst," Macromolecules, 2002, vol. 35, No. 4, 1143-1145.
Doring et al., "Scandium Aminopyridinates: Synthesis, Structure and Isoprene Polymerization," European Journal of Inorganic Chemistry, 2009, No. 28, pp. 4255-4264.
U.S. Appl. No. 15/083,479, filed Mar. 29, 2016.
Piers, et al., "Synthesis and Characterization of Mono-(pentamethylcyclopentadienyl)alkoxyscandium Alkyl Derivatives, (eta<5>-C5Me5) (OR) ScR'," Journal of Organometallic Chemistry, Elsevier-Sequoia S.A., Lausanne, CH, Apr. 9, 1991, vol. 407, No. 1, pp. 51-60.
Schaverien, et al., "Alkoxides as Ancillary Ligands in Organolanthanide Chemistry: Synthesis of, Reactivity of, and Olefin Polymerization by the Mu-hydride-mu-alkyl Compounds not Y(C5ME5) (OC6H3BU2) 3/4 2 (MU-H) (MU-Alkyl)," Organometallics, American Chemical Society, Jan. 1, 1994, vol. 13, No. 1, pp. 69-82.
Robert et al., "Neutral and Monocationic Half-Sandwich Methyl Rare-Earth Metal Complexes: Synthesis, Structure, and 1,3-Butadiene Polymerization Catalysis," European Journal of Inorganic Chemistry-Chemische Berichte, Jun. 1, 2008, vol. 2008, No. 18, pp. 2801-2809.
Lei et al., "Synthesis, Characterization of Cationic Half-sandwich Scandium Mono(silylamide) Complexes and Their Unexpected Reactivity Toward C—Cl[sigma] bond activation of chlorobenzene," Journal of Organometallic Chemistry, Oct. 1, 2014, vol. 769, pp. 119-123.
Doring et al., European Journal of Inorganic Chemistry, 2010, pp. 2853-2860.
Fischbach et al., "Synthesis and Derivatization of Halflanthanidocene aryl(alk)oxide Complexes," Inorganica Chimica Acta, 2006, vol. 359, No. 15, pp. 4855-4864.

* cited by examiner (Continued)

*Primary Examiner* — Fred M Teskin

(57) ABSTRACT

This invention relates to a process to using dimers of a group 3 metal (typically scandium) catalyst compound to produce ethylene polymers, such as ethylene-alpha-olefin copolymers and ethylene-conjugated diene copolymers.

38 Claims, No Drawings

GROUP 3 METAL CATALYST SYSTEM AND PROCESS TO PRODUCE ETHYLENE POLYMERS THEREWITH

PRIORITY CLAIM

This application claims priority to and the benefit of U.S. Ser. No. 62/393,464, filed Sep. 12, 2016 and is incorporated by reference in its entirety.

FIELD OF THE INVENTION

This invention relates to a process to produce ethylene polymers, such as ethylene homopolymers, ethylene alpha-olefin copolymers, and/or ethylene conjugated diene (such as ethylene isoprene) copolymers using a scandium catalyst compound and the copolymers so produced.

BACKGROUND OF THE INVENTION

There are few catalysts that are known to be capable of copolymerizing ethylene and conjugated dienes (e.g., isoprene) using a coordination-insertion mechanism under industrially relevant conditions. The introduction of unsaturated carbon-carbon bonds into a polyolefin is of interest because this serves as, inter alia, a route to produce vulcanized and/or functionalized polymers. These polymers have numerous potential applications, including those that require adhesion to and compatibility with other materials. One potential use for such materials is as a component in tire sidewalls and treads, where compatibility and co-curability with other tire materials (e.g., natural rubber, styrene-butadiene rubber, and cis-polybutadiene) is desirable.

Polyisoprene homopolymers and polyethylene homopolymers were prepared by Doring, Kretschmer, and Kempe in the European Journal of Inorganic Chemistry 2010, pp. 2853-2860 using various aminopyridinate complexes; however, ethylene-isoprene copolymers are not disclosed.

Ethylene-isoprene copolymers are also relatively rare. U.S. Pat. No. 6,288,191 discloses the production of ethylene-isoprene random copolymers using a cyclopentadienyl-based titanium catalyst system, where the copolymers have high 1,4 isoprene isomer content.

J. Am. Chem. Soc., 2009, 131, pp. 13870-13882, discloses the production of ethylene-isoprene random copolymers using a cyclopentadienyl-based scandium catalyst system.

Catal. Sci. Technology, 2012, 2, pp. 2090-2098, discloses the production of ethylene-isoprene copolymer using a cyclopentadienyl-titanium catalyst system where the copolymer has a melt peak at or above 133° C.

Eur. Polym. J., 1997, 33, 4, pp. 447-451, discloses the production of ethylene-isoprene copolymer using a zirconocene catalyst system, where the copolymer contains low content of isoprene and a high melting point of 119° C.

Polymer, 2008, 49, pp. 2039-2045, discloses the production of ethylene-isoprene copolymer using a neodymocene catalyst system where the copolymer has high isoprene content.

J. Polym. Sci. A, 2010, 48, pp. 4200-4206, discloses copolymerization of ethylene with isoprene promoted by titanium complexes containing a tetradentate [OSSO]-type bis(phenolato) ligand, where the copolymers have high 1,4 isoprene isomer content.

Journal of Organometallic Chemistry, 1991, 407, 51-60 discloses scandium-penta methylcyclopentadienyl-alkoxide dimers: [Cp*(Me)Sc (μ-O-3,5-di-t-Bu Ph)$_2$]$_2$ which is inert to olefins.

Other references of interest include: Macromol Chem Phys., 2001, 202, pp. 2485-2488; Macromolecules, 2002, 35, 1143-1145; JP-B-48-56775; US 2014/0018493; US 2014/0005327; US 2013/0197174; U.S. Ser. No. 15/083,479, filed Mar. 29, 2016; and European Journal of Inorganic Chemistry 2009, pp. 4255-4264.

There is still a need in the art for new and improved catalysts capable of producing ethylene polymers and in particular ethylene copolymers with conjugated dienes, including isoprene. Catalysts capable of producing high molecular weight ethylene polymer under industrially relevant conditions are desired. Highly productive catalysts are desired. Catalysts capable of producing ethylene-isoprene copolymer with low levels of 1,4-isoprene insertions relative to 3,4-insertions are also desired.

It is, therefore, an object of the present invention to provide a process to produce ethylene conjugated diene copolymers with excellent molecular weight (Mw) and polydispersity (Mw/Mn) using a family of Group 3 transition metal (preferably Sc or Y) catalysts at industrially relevant temperatures and pressures.

It is also an object of the present invention to provide a process to produce ethylene alpha olefin copolymers with excellent molecular weight (Mw) and polydispersity (Mw/Mn) using a family of Group 3 transition metal (preferably Sc or Y) catalysts at industrially relevant temperatures and pressures.

SUMMARY OF THE INVENTION

This invention relates to a catalyst compound represented by the formula (I):

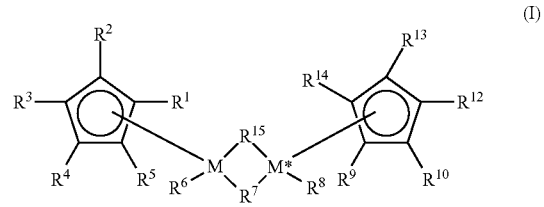

where M is a group 3 metal, such as scandium or yttrium;
M* is a group 3 metal, such as scandium or yttrium;
each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form cyclic fused ring systems, such as indene or fluorene;
each $R^7$ and $R^{15}$ is, independently, —O(R*)—, where R* is hydrogen, halogen, linear hydrocarbyl, or substituted hydrocarbyl, or -E(R)$_n$—, where E is carbon, silicon, germanium, nitrogen, phosphorus, sulfur, or halogen, such as fluorine, chlorine, bromine, or iodine; n is 0, 1, 2, or 3; each R is independently hydrogen, halogen, hydrocarbyl, or substituted hydrocarbyl; preferably when E is C, Si, or Ge, then n is 2 or 3; when E is N or P, then n is 2; when E is S, then n is 1; and when E is halogen, then n is 0; and
each $R^6$ and $R^8$ is, independently, a hydrogen, halogen, hydrocarbyl, substituted hydrocarbyl, or silylcarbyl.

This invention also relates to a process to produce polymers comprising ethylene and optionally olefins, such as conjugated diene (such as isoprene) or $C_3$ to $C_{20}$ alpha olefins (such as hexene), comprising: contacting ethylene and optional comonomer with a catalyst system comprising an activator and a catalyst compound represented by the formula (II):

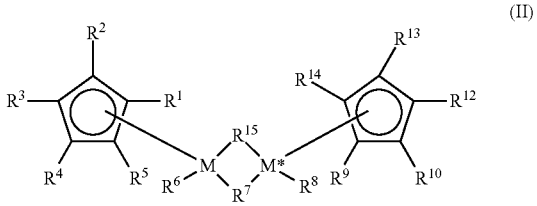

(II)

where M is a group 3 metal, such as scandium or yttrium;
M* is a group 3 metal, such as scandium or yttrium;
each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form cyclic fused ring systems, such as indene or fluorene;
each $R^7$ and $R^{15}$ is, independently, -E(R)$_n$—, where E is carbon, silicon, germanium, nitrogen, oxygen, phosphorus, sulfur, or halogen, such as fluorine, chlorine, bromine, or iodine; n is 0, 1, 2, or 3; each R is independently hydrogen, halogen, hydrocarbyl, or substituted hydrocarbyl; preferably when E is C, Si, or Ge, then n is 2 or 3; when E is N or P, then n is 2; when E is O or S, then n is 1; and when E is halogen, then n is 0; and
each $R^6$ and $R^8$ is, independently, a hydrogen, halogen, hydrocarbyl, substituted hydrocarbyl, or silylcarbyl.

This invention further relates to polymer compositions produced by the methods described herein.

In an embodiment, the process above produces a polymer comprising ethylene and optional comonomer.

In an embodiment, the process above produces a copolymer comprising ethylene and conjugated diene, preferably an ethylene isoprene copolymer, having:
1) from 75 mol % to 99 mol % ethylene;
2) from 1 mol % to 25 mol % conjugated diene, preferably isoprene; and
3) where the mol % amount of the mer unit derived from the conjugated diene where one double bond is incorporated into the copolymer backbone, leaving a pendant double bond, is present at least 1.5 times higher than the mol % amount of the mer unit derived from the conjugated diene where both double bonds are incorporated into the copolymer backbone.

In an embodiment, the process above produces a copolymer comprising ethylene isoprene comprising from 75 mol % to 99 mol % ethylene and from 1 mol % to 25 mol % isoprene, where the 3,4 isoprene isomer mol % content in the copolymer is at least 1.5 times higher than the 1,4 isomer mol % content in the copolymer.

In an embodiment, the process above produces a copolymer comprising ethylene and alpha olefin, preferably an ethylene hexene copolymer, having from 65 mol % to 99.9 mol % ethylene and 0.1 mol % to 35 mol % hexene.

Definitions

For the purposes of this invention and the claims thereto, the new numbering scheme for the Periodic Table Groups is used as described in CHEMICAL AND ENGINEERING NEWS, 63(5), pg. 27 (1985). Therefore, a "Group 4 metal" is an element from Group 4 of the Periodic Table, e.g., Hf, Ti, or Zr.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

For the purposes of this invention, ethylene shall be considered an α-olefin.

For the purposes of this invention and claims thereto, unless otherwise indicated, the term "aryl" or "aryl group" means an aromatic hydrocarbyl radical, preferably an aromatic cyclic structure having five or six members, such as the $C_6H_5$ radical, which is typically called phenyl. Aryl groups also include the derivatives of phenyl in which one to five of the hydrogen atoms have been replaced by additional hydrocarbyl groups. For example, aryls include groups such as 2,6-diisopropylphenyl, 2,4,6-trimethylphenyl, 2,3,4,5,6-pentamethylphenyl, 2-phenyl-4-methylphenyl, and the like.

For the purposes of this invention and claims thereto, unless otherwise indicated, the term "heteroatom" means a group 13, 14, 15, 16, or 17 non-metal element that is not carbon. Typical heteroatoms include nitrogen, oxygen, silicon, phosphorous, sulfur, fluorine, chlorine, bromine, and iodine.

For purposes of this invention and claims thereto, unless otherwise indicated, the term "substituted" means that a hydrogen group has been replaced with a heteroatom or a heteroatom-containing group.

The terms "hydrocarbyl radical," "hydrocarbyl" and "hydrocarbyl group" are used interchangeably throughout this document. Likewise the terms "group," "radical," and "substituent" are also used interchangeably in this document. For purposes of this disclosure, "hydrocarbyl radical" is defined to be radicals consisting of carbon and hydrogen, preferably $C_1$-$C_{100}$ radicals, that may be linear, branched, or cyclic, and when cyclic, aromatic or non-aromatic, and a "substituted hydrocarbyl" is a radical made of carbon and hydrogen where at least one hydrogen is replaced by a heteroatom or heteroatom-containing group, such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N($R^*$)—, =N—, —P($R^*$)—, =P—, —As($R^*$)—, =As—, —Sb($R^*$)—, =Sb—, —B($R^*$)—, =B—, —Si($R^*$)$_2$—, —Ge($R^*$)$_2$—, —Sn($R^*$)$_2$—, —Pb($R^*$)$_2$—, and the like, where $R^*$ is independently a hydrocarbyl or halocarbyl radical, and two or more $R^*$ may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where $R^*$ is independently a hydrocarbyl or halocarbyl radical and two or more $R^*$ may join together to form a substituted or unsubstituted saturated, partially unsaturated or aromatic cyclic or polycyclic ring structure.

For purposes of this invention and claims thereto in relation to the transition metal compounds described herein, the term "substituted" means that a hydrogen has been replaced with a hydrocarbyl group, a heteroatom, or a heteroatom-containing group. An example of a "cyclopentadiene" is 2-phenylcyclopentadiene, which is a cyclopentadiene that has been substituted at the 2 position with a phenyl group.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) are g/mol. The following abbreviations may be used herein: Me is methyl, Et is ethyl, Pr is propyl, n-Pr is n-propyl, iPr is isopropyl, Bu is butyl, iBu is isobutyl, sBu is sec-butyl, tBu is tert-butyl, Oct is octyl, Ph is phenyl, Bn is benzyl, THF or thf is tetrahydrofuran, Cp* is pentamethylcyclopentadienyl, and MAO is methylalumoxane.

A "catalyst system" is a combination of at least one catalyst compound, at least one activator, an optional co-activator, and an optional support material. For the purposes of this invention and the claims thereto, when catalyst systems are described as comprising neutral stable forms of the components, it is well understood by one of ordinary skill in the art, that the ionic form of the component is the form that reacts with the monomers to produce polymers. A polymerization catalyst system is a catalyst system that can polymerize monomers to polymer.

In the description herein, the catalyst may be described as a catalyst precursor, a pre-catalyst compound, a scandium catalyst compound or a transition metal compound, and these terms are used interchangeably.

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties.

Room temperature is 23° C. unless otherwise noted.

By 1,4 isoprene isomer is meant that when the isoprene is incorporated into the polymer chain, the microstructure of the isoprene derived unit is represented by one or both of the formulae:

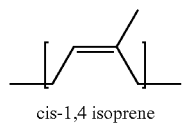 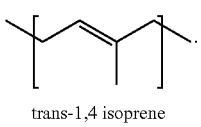
cis-1,4 isoprene     trans-1,4 isoprene

By 1,2 isoprene isomer is meant that when the isoprene is incorporated into the polymer chain, the microstructure of the isoprene derived unit is represented by the formula:

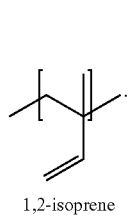
1,2-isoprene

By 3,4 isoprene isomer is meant that when the isoprene is incorporated into the polymer chain, the microstructure of the isoprene derived unit is represented by the formula:

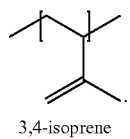
3,4-isoprene

Polymer microstructure is determined by $^1$H NMR as described below.

DETAILED DESCRIPTION OF THE INVENTION

This invention relates to group 3 catalyst compounds represented by the formula (I):

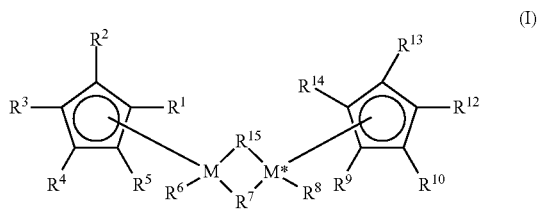

(I)

where M is a group 3 metal, such as scandium or yttrium, preferably Sc;

M* is a group 3 metal, such as scandium or yttrium, preferably Sc;

each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form cyclic fused ring systems, such as indene or fluorene;

each $R^7$ and $R^{15}$ is, independently, —O($R^*$)—, where $R^*$ is hydrogen, halogen, linear hydrocarbyl, or substituted hydrocarbyl, or -E(R)$_n$—, where E is carbon, silicon, germanium, nitrogen, phosphorus, oxygen, sulfur, or halogen, such as fluorine, chlorine, bromine, or iodine; n is 0, 1, 2, or 3; each R is independently hydrogen, halogen, hydrocarbyl, or substituted hydrocarbyl; preferably when E is C, Si, or Ge, then n is 2 or 3; when E is N or P, then n is 2; when E is S, then n is 1; and when E is halogen, then n is 0; and each $R^6$ and $R^8$ is, independently, a hydrogen, halogen, hydrocarbyl, or substituted hydrocarbyl.

This invention also relates to catalysts systems comprising activators and group 3 catalyst compounds and a process to produce polymers comprising ethylene and optional comonomer (such as olefins including conjugated dienes (such as isoprene) and/or $C_3$ to $C_{20}$ olefins (such as hexene)) comprising: 1) contacting ethylene and optional comonomer with the catalyst system and 2) obtaining polymer; where the catalyst system comprises an activator and a catalyst compound represented by the formula (II):

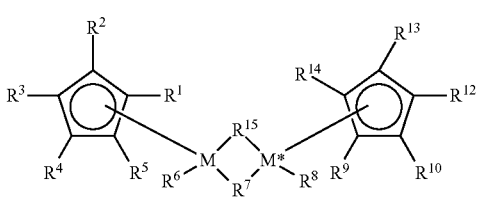

where M is a group 3 metal, such as scandium or yttrium, preferably Sc;
M* is a group 3 metal, such as scandium or yttrium, preferably Sc;
each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form cyclic fused ring systems, such as indene or fluorene;
each $R^7$ and $R^{15}$ is, independently, $-E(R)_n-$, where E is carbon, silicon, germanium, nitrogen, phosphorus, oxygen, sulfur, or halogen, such as fluorine, chlorine, bromine, or iodine; n is 0, 1, 2, or 3; each R is independently hydrogen, halogen, hydrocarbyl, or substituted hydrocarbyl; preferably when E is C, Si, or Ge, then n is 2 or 3; when E is N or P, then n is 2; when E is O or S, then n is 1; and when E is halogen, then n is 0; and
each $R^6$ and $R^8$ is, independently, a hydrogen, halogen, hydrocarbyl, substituted hydrocarbyl, or silylcarbyl.

This invention also relates to a catalyst compound represented by the formula (II):

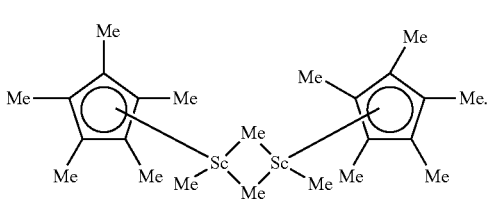

This invention also relates to a process to produce polymers comprising ethylene comprising: 1) contacting ethylene and optional comonomer with a catalyst system comprising an activator and a catalyst compound represented by the formula (II):

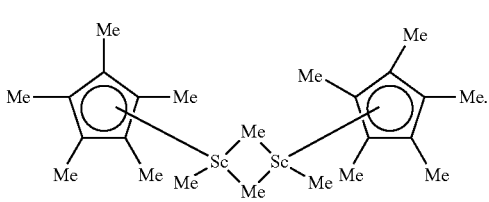

In a useful embodiment, the catalyst system, activator, and/or the catalyst compound is supported on a support, such as silica. Typically, the catalyst compound and the activator are supported on silica.

The process described herein produces homopolymers and/or copolymers of ethylene.

In an embodiment, the process above produces a copolymer comprising ethylene and conjugated diene, preferably an ethylene isoprene copolymer, having:

1) from 75 mol % to 99 mol % ethylene, preferably 80 mol % to 98 mol %, preferably 90 mol % to 98 mol %;
2) from 1 mol % to 25 mol % conjugated diene, preferably isoprene, preferably 2 mol % to 20 mol %, preferably 2 mol % to 10 mol %; and
where the mol % amount of the mer unit derived from the conjugated diene where one double bond is incorporated into the copolymer backbone, leaving a pendant double bond, is present at least 1.5 times higher than the mol % amount of the mer unit derived from the conjugated diene where both double bonds are incorporated into the copolymer backbone, alternately at least 1.75 times higher, alternately at least 2 times higher, alternately at least 3 times higher, alternately at least 4 times higher, alternately at least 5 times higher, alternately at least 6 times higher, alternately at least 10 times higher, alternately at least 11 times higher.

In an embodiment, the process above produces a copolymer comprising ethylene and conjugated diene, preferably an ethylene isoprene copolymer, having:

1) from 75 mol % to 99 mol % ethylene, preferably 80 mol % to 98 mol %, preferably 90 mol % to 98 mol %;
2) from 1 mol % to 25 mol % isoprene, preferably 2 mol % to 20 mol %, preferably 2 mol % to 10 mol %; and
3) where the 3,4 isoprene isomer mol % content is at least 1.5 times higher than the 1,4 isomer mol % content, alternately at least 1.75 times higher, alternately at least 2 times higher, alternately at least 3 times higher, alternately at least 4 times higher, alternately at least 5 times higher, alternately at least 6 times higher, alternately at least 10 times higher, alternately at least 11 times higher.

In an embodiment, the process above produces a copolymer comprising ethylene and alpha olefin, preferably an ethylene hexene copolymer, having from 65 mol % to 99.9 mol % ethylene (preferably 80 mol % to 99 mol %, preferably 90 mol % to 98 mol %) and 0.1 mol % to 35 mol % hexene (preferably 1 mol % to 20 mol %, preferably 2 mol % to 10 mol %).

Catalyst Compounds

This invention relates to transition metal complexes useful herein as catalyst components comprising dimers of cyclopentadienyl group 3 transition metal (scandium and/or yttrium) complexes.

In a preferred embodiment of the invention, the transition metal complex is a dimer of a scandium complex where each scandium is coordinated by a pentamethylcyclopentadienyl ligand, as well as one terminal methyl group and two methyl groups that bridge to the other scandium.

In a preferred embodiment of the invention, the catalyst compound useful herein is represented by the formula (I):

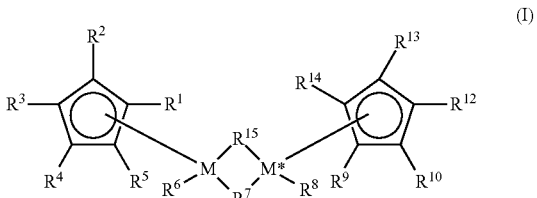

where M is a group 3 metal, such as scandium or yttrium, preferably Sc;
M* is a group 3 metal, such as scandium or yttrium, preferably Sc;

each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form cyclic fused ring systems, such as indene or fluorene;

each $R^7$ and $R^{15}$ is, independently, —O(R*)—, where R* is hydrogen, halogen, linear hydrocarbyl, or substituted hydrocarbyl, or -E(R)$_n$—, where E is carbon, silicon, germanium, nitrogen, phosphorus, sulfur, or halogen, such as fluorine, chlorine, bromine, or iodine; n is 0, 1, 2, or 3; each R is independently hydrogen, halogen, hydrocarbyl, or substituted hydrocarbyl; preferably when E is C, Si, or Ge, then n is 2 or 3; when E is N or P, then n is 2; when E is S, then n is 1; and when E is halogen, then n is 0;

each $R^6$ and $R^8$ is, independently, a hydrogen, halogen, hydrocarbyl, substituted hydrocarbyl, or silylcarbyl.

This invention also relates to catalyst compounds useful in a catalyst system for polymerization of olefins represented by the formula (II):

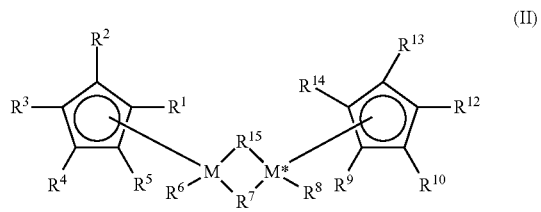

(II)

where M is a group 3 metal, such as scandium or yttrium, preferably Sc;

M* is a group 3 metal, such as scandium or yttrium, preferably Sc;

each $R^1$, $R^2$, $R^3$, $R^4$, $R^5$, $R^9$, $R^{10}$, $R^{11}$, $R^{12}$, $R^{13}$, and $R^{14}$ is, independently, hydrogen, a hydrocarbyl, or a substituted hydrocarbyl, where adjacent R groups optionally form cyclic fused ring systems, such as indene or fluorene;

each $R^7$ and $R^{15}$ is, independently, -E(R)$_n$—, where E is carbon, silicon, germanium, nitrogen, phosphorus, oxygen, sulfur, or halogen, such as fluorine, chlorine, bromine, or iodine; n is 0, 1, 2, or 3; each R is independently hydrogen, halogen, hydrocarbyl, or substituted hydrocarbyl; preferably when E is C, Si, or Ge, then n is 2 or 3; when E is N or P, then n is 2; when E is O or S, then n is 1; and when E is halogen, then n is 0;

each $R^6$ and $R^8$ is, independently, a hydrogen, halogen, hydrocarbyl, substituted hydrocarbyl, or silylcarbyl.

In any embodiment of the invention described herein, M may be Sc or Y, preferably Sc. In any embodiment of the invention described herein, M* may be Sc or Y, preferably Sc. M and M* may be the same or different. In any embodiment of the invention described herein, M and M* are Sc.

In any embodiment of the invention described herein, each $R^1$, $R^2$, $R^3$, $R^4$, $R^5$, $R^9$, $R^{10}$, $R^{12}$, $R^{13}$, and $R^{14}$ is selected from $C_1$ to $C_{30}$ alkyls, $C_1$ to $C_{30}$ alkylsilanes, preferably $C_1$ to $C_8$ alkyls, $C_1$ to $C_7$ alkylsilanes, such as: methyl, ethyl, propyl, butyl, pentyl, hexyl, heptyl, octyl, nonyl, decyl, undecyl, dodecyl, $CH_2SiMe_3$, benzyl, $CH_2CMe_3$, $CH(SiMe_3)_2$, $CH_2SiPh_3$, and $CH_2CMe_2Ph$ and isomers thereof.

In any embodiment of the invention described herein, each $R^6$ and $R^8$ is selected from methyl, ethyl, propyl, butyl, pentyl, hexyl, heptyl, octyl, nonyl, decyl, undecyl, dodecyl, isomers thereof, chloro, iodo, bromo and fluoro.

In any embodiment of the invention described herein, each $R^6$ and $R^8$ is selected from $SiMe_3$, $SiPh_3$, and $CH_2SiMe_3$, $CH_2SiPh_3$, $CH_2SiMe_2Ph$, $CH_2SiMePh_2$, $CH(SiMe_3)_2$.

In any embodiment of the invention described herein, E is carbon.

In any embodiment of the invention described herein, each R is, independently, hydrogen, methyl, methyl, ethyl, propyl, butyl, pentyl, hexyl, heptyl, octyl, nonyl, decyl, undecyl, dodecyl, or an isomer thereof, $CH_2SiMe_3$, benzyl, $CH_2CMe_3$, $CH(SiMe_3)_2$, $CH_2SiPh_3$, or $CH_2CMe_2Ph$.

In any embodiment of the invention described herein, each $R^7$ and $R^{15}$ is, independently, —C(R)$_n$—, n is 2, or 3; and each R is independently hydrogen, halogen (Cl, Br, I, or F), hydrocarbyl (preferably $C_1$ to $C_{20}$ hydrocarbyl), or substituted hydrocarbyl (preferably $C_1$ to $C_{20}$ substituted hydrocarbyl), alternately each R is independently hydrogen, Cl, Br, F, methyl, ethyl, propyl, butyl, pentyl, hexyl, heptyl, octyl, nonyl, decyl, undecyl, dodecyl, or an isomer thereof, $CH_2SiMe_3$, benzyl, $CH_2CMe_3$, $CH(SiMe_3)_2$, $CH_2SiPh_3$, or $CH_2CMe_2Ph$.

In any embodiment of the invention described herein, each $R^1$, $R^2$, $R^3$, $R^4$, $R^5$, $R^9$, $R^{10}$, $R^{11}$, $R^{12}$, $R^{13}$, and $R^{14}$ is, independently, hydrogen, methyl, methyl, ethyl, propyl, butyl, pentyl, hexyl, heptyl, octyl, nonyl, decyl, undecyl, dodecyl, $CH_2SiMe_3$, benzyl, $CH_2CMe_3$, $CH(SiMe_3)_2$, $CH_2SiPh_3$, $CH_2CMe_2Ph$ or an isomer thereof and $R^6$ and $R^8$ are methyl, ethyl, propyl, butyl, pentyl, hexyl, heptyl, octyl, nonyl, decyl, undecyl, dodecyl, isomers thereof, chloro, iodo, bromo and fluoro.

Catalyst compounds useful herein include:
bis pentamethylcyclopentadienyl yttrium dimethyl; bis pentamethylcyclopentadienyl scandium dimethyl; bis pentamethylcyclopentadienyl scandium diethyl; bis tetramethylcyclopentadienyl scandium dimethyl; bis tetramethylcyclopentadienyl scandium diethyl; bis cyclopentadienyl scandium dimethyl; bis cyclopentadienyl scandium diethyl; bis indenyl scandium dimethyl; bis indenyl scandium diethyl; bis 2-methylindenyl scandium dimethyl; bis 2-methylindenyl scandium diethyl; bis 2-methyl-4-phenylindenyl scandium dimethyl; bis 2-methyl-4-phenylindenyl scandium diethyl; bis fluorenyl scandium dimethyl; bis fluorenyl scandium diethyl; bis pentamethylcyclopentadienyl yttrium diethyl; bis tetramethylcyclopentadienyl yttrium dimethyl; bis tetramethylcyclopentadienyl yttrium diethyl; bis cyclopentadienyl yttrium dimethyl; bis cyclopentadienyl yttrium diethyl; bis indenyl yttrium dimethyl; bis indenyl yttrium diethyl; bis 2-methylindenyl yttrium dimethyl; bis 2-methylindenyl yttrium diethyl; bis 2-methyl-4-phenylindenyl yttrium dimethyl; bis 2-methyl-4-phenylindenyl yttrium diethyl; bis fluorenyl yttrium dimethyl; bis fluorenyl yttrium diethyl; bis pentamethylcyclopentadienyl lutetium diethyl; bis pentamethylcyclopentadienyl lutetium diethyl; bis tetramethylcyclopentadienyl lutetium dimethyl; bis tetramethylcyclopentadienyl lutetium diethyl; bis cyclopentadienyl lutetium dimethyl; bis cyclopentadienyl lutetium diethyl; bis indenyl lutetium dimethyl; bis indenyl lutetium diethyl; bis 2-methylindenyl lutetium dimethyl; bis 2-methylindenyl lutetium diethyl; bis 2-methyl-4-phenylindenyl lutetium dimethyl; bis 2-methyl-4-phenylindenyl lutetium diethyl; bis fluorenyl lutetium dimethyl; bis fluorenyl lutetium diethyl.

In a preferred embodiment of the invention in any of the processes described herein, one catalyst compound is used, e.g., the catalyst compounds are not different. For purposes of this invention one catalyst compound is considered different from another if they differ by at least one atom.

In some embodiments, two or more different catalyst compounds are present in the catalyst system used herein. In some embodiments, two or more different catalyst compounds are present in the reaction zone where the process(es) described herein occur. When two transition metal compound based catalysts are used in one reactor as a mixed catalyst system, the two transition metal compounds are preferably chosen such that the two are compatible. It is preferable to use the same activator for the transition metal compounds, however, two different activators, such as a non-coordinating anion activator and an alumoxane, can be used in combination. If one or more transition metal compounds contain an $R^6$ and/or $R^8$ ligand which is not a hydride, hydrocarbyl, or substituted hydrocarbyl, then an alkylating reagent such as alumoxane or trialkylaluminum can be contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1,000 to 1,000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10% to 99.9% A to 0.1% to 90% B, alternatively 25% to 99% A to 0.5% to 50% B, alternatively 50% to 99% A to 1% to 25% B, and alternatively 75% to 99% A to 1% to 10% B.

Methods to Prepare the Catalyst Compounds

Transition metal complexes useful as catalyst components herein may be typically prepared by treating a metal salt (e.g., scandium tris(acetylacetonate) with the alkali salt of cyclopentadienide coordinating group (e.g., lithium pentamethylcyclopentadienide), and treating the resultant bis(acetylacetonate) complex with a halogenating agent to obtain a scandium dichloride cyclopentadienide complex. This complex can be treated with an alkylating agent to obtain a scandium dimer that can be used as a catalyst component.

Activators

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

In one embodiment, alumoxane activators are utilized as an activator in the catalyst composition. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

When the activator is an alumoxane (modified or unmodified), some embodiments select the maximum amount of activator typically at up to a 5,000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mol %, alternately the alumoxane is present at a molar ratio of aluminum to catalyst compound transition metal less than 500:1, preferably less than 300:1, preferably less than 100:1, preferably less than 1:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral activator is tris perfluorophenyl boron or tris perfluoronaphthyl boron.

Ionic activator compounds may contain an active proton, or some other cation associated with, but not coordinated to, or only loosely coordinated to, the remaining ion of the ionizing compound. Such compounds and the like are described in EP 0 570 982A; EP 0 520 732 A; EP 0 495 375 A; EP 0 500 944 BI; EP 0 277 003 A; EP 0 277 004 A; U.S. Pat. Nos. 5,153,157; 5,198,401; 5,066,741; 5,206,197; 5,241,025; 5,384,299; 5,502,124; and U.S. Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation), which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277 003 A1 and EP 0 277 004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment of the invention, the activators include a cation and an anion component, and are preferably represented by the following formula (II):

$$(Z)_d^+(A^{d-}) \qquad (II)$$

wherein Z is (L-H) or a reducible Lewis Acid, L is a neutral Lewis base; H is hydrogen; (L-H)$^+$ is a Bronsted acid; A$^{d-}$ is a non-coordinating anion having the charge d–; and d is an integer from 1 to 3.

When Z is (L-H) such that the cation component is (L-H)$_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation (L-H)$_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether, diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl, preferably the reducible Lewis acid is represented by the formula: (Ph$_3$C$^+$), where Ph is phenyl or phenyl substituted with a heteroatom, a C$_1$ to C$_{40}$ hydrocarbyl, or a substituted C$_1$ to C$_{40}$ hydrocarbyl. In a preferred embodiment of the invention, the reducible Lewis acid is triphenyl carbenium.

The anion component A$^{d-}$ include those having the formula [M$^{k+}$Q$_n$]$^{d-}$ wherein k is 1, 2, or 3; n is 1, 2, 3, 4, 5, or 6, preferably 3, 4, 5, or 6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable A$^{d-}$ components also include diboron compounds as disclosed in U.S. Pat. No. 5,447,895, which is fully incorporated herein by reference.

In a preferred embodiment of the invention, this invention relates to a method to polymerize olefins comprising contacting olefins (preferably ethylene and/or propylene) with the catalyst compound, an optional chain transfer agent and a boron containing NCA activator represented by the formula (14):

$$Z_d^+(A^{d-}) \qquad (14)$$

where: Z is (L-H) or a reducible Lewis acid; L is a neutral Lewis base (as further described above); H is hydrogen; (L-H) is a Bronsted acid (as further described above); A$^{d-}$ is a boron containing non-coordinating anion having the charge d$^-$ (as further described above); d is 1, 2, or 3.

In a preferred embodiment of the invention in any NCA's represented by Formula 14 described above, the reducible Lewis acid is represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl, preferably the reducible Lewis acid is represented by the formula: (Ph$_3$C$^+$), where Ph is phenyl or phenyl substituted with a heteroatom, a C$_1$ to C$_{40}$ hydrocarbyl, or a substituted C$_1$ to C$_{40}$ hydrocarbyl.

In a preferred embodiment of the invention in any of the NCA's represented by Formula 14 described above, Z$_d^+$ is represented by the formula: (L-H)$_d^+$, wherein L is a neutral Lewis base; H is hydrogen; (L-H) is a Bronsted acid; and d is 1, 2, or 3, preferably (L-H)$_d^+$ is a Bronsted acid selected from ammoniums, oxoniums, phosphoniums, silyliums, and mixtures thereof.

In a preferred embodiment of the invention in any of the NCA's represented by Formula 14 described above, the anion component A$^{d-}$ is represented by the formula [M*$^{k*}$+Q*$_{n*}$]$^{d*-}$ wherein k* is 1, 2, or 3; n* is 1, 2, 3, 4, 5, or 6 (preferably 1, 2, 3, or 4); n*–k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene and/or propylene) with the catalyst compound, an optional chain transfer agent and an NCA activator represented by the formula (I):

$$R_nM^{**}(ArNHal)_{4-n} \qquad (I)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula I also comprises a suitable cation that is essentially noninterfering with the ionic catalyst complexes formed with the transition metal compounds, preferably the cation is $Z_d^+$ as described above.

In a preferred embodiment of the invention in any of the NCA's comprising an anion represented by Formula I described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; —$SR^1$, —$NR^2_2$, and —$PR^3_2$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment of the invention in any of the NCA's comprising an anion represented by Formula I described above, the NCA also comprises cation comprising a reducible Lewis acid represented by the formula: ($Ar_3C^+$), where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid represented by the formula: ($Ph_3C^+$), where Ph is phenyl or phenyl substituted with a heteroatom, a $C_1$ to $C_{40}$ hydrocarbyl, or a substituted $C_1$ to $C_{40}$ hydrocarbyl.

In a preferred embodiment of the invention in any of the NCA's comprising an anion represented by Formula I described above, the NCA also comprises a cation represented by the formula, $(L-H)_d^+$, wherein L is a neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

Further examples of useful activators include those disclosed in U.S. Pat. Nos. 7,297,653 and 7,799,879.

Another activator useful herein comprises a salt of a cationic oxidizing agent and a noncoordinating, compatible anion represented by the formula (16):

$$(OX^{e+})_d(A^{d-})_e \quad (16)$$

wherein $OX^{e+}$ is a cationic oxidizing agent having a charge of e+; e is 1, 2, or 3; d is 1, 2, or 3; and $A^{d-}$ is a non-coordinating anion having the charge of d− (as further described above). Examples of cationic oxidizing agents include: ferrocenium, hydrocarbyl-substituted ferrocenium, $Ag^+$, or $Pb^{+2}$. Preferred embodiments of $A^{d-}$ include tetrakis(pentafluorophenyl)borate.

In another embodiment, the amidinate catalyst compounds and optional CTA's described herein can be used with Bulky activators. A "Bulky activator" as used herein refers to anionic activators represented by the formula:

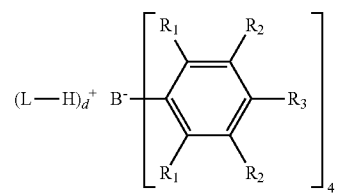

where: each $R_1$ is, independently, a halide, preferably a fluoride; each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);

each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring); L is a neutral Lewis base; $(L-H)^+$ is a Bronsted acid; d is 1, 2, or 3; wherein the anion has a molecular weight of greater than 1020 g/mol; and wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple 'Back of the Envelope' Method for Estimating the Densities and Molecular Volumes of Liquids and Solids," Journal of Chemical Education, Vol. 71, No. 11, November, 1994, pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
| --- | --- |
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | $V_S$ | MV Per subst. (Å³) | Total MV (Å³) |
|---|---|---|---|---|---|
| Dimethylanilinium tetrakis(perfluoronaphthyl)borate | [perfluoronaphthyl structure]₄ | $C_{10}F_7$ | 34 | 261 | 1044 |
| Dimethylanilinium tetrakis(perfluorobiphenyl)borate | [perfluorobiphenyl structure]₄ | $C_{12}F_9$ | 42 | 349 | 1396 |
| [4-tButyl-PhNMe₂H] [$(C_6F_3(C_6F_5)_2)_4B$] | [perfluoroterphenyl structure]₄ | $C_{18}F_{13}$ | 62 | 515 | 2060 |

Exemplary bulky activators useful in catalyst systems herein include: trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl) ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, [4-t-butyl-PhNMe₂H] [$(C_6F_3(C_6F_5)_2)_4B$], and the types disclosed in U.S. Pat. No. 7,297,653.

Illustrative, but not limiting, examples of boron compounds which may be used as an activator in the processes of this invention are: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl) ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl) ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenyiphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl) ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenyiphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl) ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenyiphosphonium tetrakis(perfluorobiphenyl)borate, triethylsilylium tetrakis(perfluorobiphenyl)borate, benzene(diazonium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenyiphosphonium tetrakis(3,5-bis(trifluoromethyl)phenyl)borate, triethylsilylium tetrakis(3,5-bis(trifluoromethyl)phenyl)borate, benzene(diazonium) tetrakis(3,5-bis(trifluoromethyl)phenyl)borate, and dialkyl ammonium salts, such as: di-(i-propyl)ammonium tetrakis(pentafluorophenyl)borate, and dicyclohexylammonium tetrakis(pentafluorophenyl)borate; and additional tri-substituted phosphonium salts, such as tri(o-tolyl)phosphonium tetrakis(pentafluorophenyl)borate, and tri(2,6-dimethylphenyl)phosphonium tetrakis(pentafluorophenyl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4^-]$, $[Me_3NH^+][B(C_6F_5)_4^-]$; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment of the invention, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

In a preferred embodiment of the invention, any of the activators described herein may be mixed together before or after combination with the catalyst compound preferably before being mixed with the catalyst compound.

In some embodiments, two NCA activators may be used in the polymerization and the molar ratio of the first NCA activator to the second NCA activator can be any ratio. In some embodiments, the molar ratio of the first NCA activator to the second NCA activator is 0.01:1 to 10,000:1, preferably 0.1:1 to 1,000:1, preferably 1:1 to 100:1.

Further, the typical activator-to-catalyst ratio, e.g., all NCA activators-to-catalyst ratio is a 1:1 molar ratio. Alternate preferred ranges include from 0.1:1 to 100:1, alternately from 0.5:1 to 200:1, alternately from 1:1 to 500:1, alternately from 1:1 to 1000:1. A particularly useful range is from 0.5:1 to 10:1, preferably 1:1 to 5:1.

Additionally, preferred activators useful herein include those described in U.S. Pat. No. 7,247,687 at column 169, line 50 to column 174, line 43, particularly column 172, line 24 to column 173, line 53.

It is also within the scope of this invention that the catalyst compounds can be combined with combinations of alumoxanes and NCA's (see for example, U.S. Pat. Nos. 5,153,157; 5,453,410; EP 0 573 120 BI; WO 94/07928; and WO 95/14044 which discuss the use of an alumoxane in combination with an ionizing activator).

Chain Transfer Agents

Useful chain transfer agents are typically alkylalumoxanes or alkylzincs, preferably a compound represented by the formula $AlR_3$, $ZnR_2$ (where each R is, independently, a $C_1$-$C_8$ aliphatic radical, preferably methyl, ethyl, propyl, butyl, penyl, hexyl octyl or an isomer thereof) or a combination thereof, such as diethyl zinc, methylalumoxane, trimethylaluminum, triisobutylaluminum, trioctylaluminum, or a combination thereof.

Optional Scavengers or Co-Activators

In addition to the above activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Optional Support Materials

In embodiments herein, the catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. Most preferably the surface area of the support material is in the range is from about 100 to about 400 $m^2/g$, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2/gm$; pore volume of 1.65 $cm^3/gm$). Preferred silicas are marketed under the tradenames of DAVISON 952 or DAVISON 955 by the Davison Chemical Division of W.R. Grace and Company. In other embodiments DAVISON 948 is used.

The support material should be dry, that is, free of absorbed water. Drying of the support material can be effected by heating or calcining at about 100° C. to about 1,000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the metallocene compound is then contacted with the isolated support/activator. In some embodiments, the supported catalyst system is generated in situ. In an alternate embodiment, the slurry of the support material is first contacted with the catalyst compound for a period of time in the range of from about 0.5 hours to about 24 hours, from about 2 hours to about 16 hours, or from about 4 hours to about 8 hours. The slurry of the supported metallocene compound is then contacted with the activator solution.

The mixture of the catalyst compound, activator and support is heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

In a particularly useful embodiment, the support material is fluorided. Fluoriding agent containing compounds may be any compound containing a fluorine atom. Particularly desirable are inorganic fluorine containing compounds are selected from the group consisting of $NH_4BF_4$, $(NH_4)_2SiF_6$, $NH_4PF_6$, $NH_4F$, $(NH_4)_2TaF_7$, $NH_4NbF_4$, $(NH_4)_2GeF_6$, $(NH_4)_2SmF_6$, $(NH_4)_2TiF_6$, $(NH_4)_2ZrF_6$, $MoF_6$, $ReF_6$, $GaF_3$, $SO_2ClF$, $F_2$, $SiF_4$, $SF_6$, $ClF_3$, $ClF_5$, $BrF_5$, $IF_7$, $NF_3$, $HF$, $BF_3$, $NHF_2$ and $NH_4HF_2$. Of these, ammonium hexafluorosilicate and ammonium tetrafluoroborate are useful. Combinations of these compounds may also be used.

Ammonium hexafluorosilicate and ammonium tetrafluoroborate fluorine compounds are typically solid particulates as are the silicon dioxide supports. A useful method of treating the support with the fluorine compound is to dry mix the two components by simply blending at a concentration of from 0.01 to 10.0 millimole F/g of support, desirably in the range of from 0.05 to 6.0 millimole F/g of support, and most desirably in the range of from 0.1 to 3.0 millimole F/g of support. The fluorine compound can be dry mixed with the support either before or after charging to a vessel for dehydration or calcining the support. Accordingly, the fluorine concentration present on the support is in the range of from 0.1 to 25 wt %, alternately 0.19 to 19 wt %, alternately from 0.6 to 3.5 wt %, based upon the weight of the support.

Polymerization Processes

In embodiments herein, the invention relates to polymerization processes where monomer comprising ethylene and optional comonomer such as conjugated diene (such as isoprene) or $C_3$ to $C_{20}$ alpha olefin (such as hexene) are contacted with a catalyst system comprising an activator and at least one catalyst compound, as described above. The catalyst compound and activator may be combined in any order, and are combined typically prior to contacting with the monomer.

Preferred comonomers useful in this invention include substituted or unsubstituted $C_3$ to $C_{40}$ alpha olefins, preferably $C_3$ to $C_{20}$ alpha olefins, preferably $C_3$ to $C_{12}$ alpha olefins, preferably propylene, butene, pentene, hexene, heptene, octene, nonene, decene, undecene, dodecene and isomers thereof. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_3$ to $C_{40}$ olefin comonomers include propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbomadiene, and dicyclopentadiene.

Preferred conjugated diene monomers useful in this invention include any hydrocarbon structure, preferably $C_4$ to $C_{30}$, having at least two unsaturated bonds that are adjacent to each other. Examples of useful conjugated dienes include isoprene, 1,3-butadiene, 1,3-pentadiene, 1,3-hexadiene, 1,3-heptadiene, 1,3-octadiene, 1,3-nonadiene, 1,3-decadiene, cyclopentadiene, dicyclopentadiene or higher ring containing diolefins with or without substituents at various ring positions.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 vol % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein, the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment of the invention, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment of the invention, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 60° C. to about 120° C., preferably from about 70° C. to about 120° C., preferably from about 75° C. to about 120° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In a preferred embodiment of the invention, little or no alumoxane is used in the process to produce the polymers. Optionally, alumoxane is present at zero mol %, alternately the alumoxane is present at a molar ratio of aluminum to transition metal less than 500:1, preferably less than 300:1, preferably less than 100:1, preferably less than 1:1.

In a preferred embodiment of the invention, little or no scavenger is used in the process to produce the ethylene polymer. Preferably, scavenger (such as trialkylaluminum) is present at zero mol %, alternately, the scavenger is present at a molar ratio of scavenger metal to transition metal of less than 100:1, preferably less than 50:1, preferably less than 15:1, preferably less than 10:1.

Other additives may also be used in the polymerization, as desired, such as one or more scavengers, promoters, modifiers, chain transfer agents (such as trialkylaluminums, triisobutylaluminum, tri(n-octyl)aluminum, diethylzinc), reducing agents, oxidizing agents, hydrogen, aluminum alkyls, or silanes.

In a particularly useful embodiment, the polymerization process is a gas phase process, such as a fluidized gas bed process. Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See, for example, U.S. Pat. Nos. 4,543,399; 4,588,790; 5,028,670; 5,317,036; 5,352,749; 5,405,922; 5,436,304; 5,453,471; 5,462,999; 5,616,661; and 5,668,228; all of which are fully incorporated herein by reference.)

In a particularly useful embodiment, the polymerization process is a slurry process. As used herein, the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers, along with catalysts, are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane (such as the solvents/diluents named above). The medium employed should be liquid under the conditions of polymerization and relatively inert. When a propane medium is used, the process is often operated above the reaction diluent critical temperature and pressure. Preferably, a hexane or an isobutane medium is employed.

Polyolefin Products

This invention also relates to compositions of matter produced by the methods described herein.

In a preferred embodiment of the invention, the process described herein produces ethylene homopolymer.

In a preferred embodiment of the invention, the process described herein produces ethylene copolymers.

In a preferred embodiment of the invention, the process described herein produces copolymers of ethylene and of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene, preferably hexene).

In a preferred embodiment, the polymers produced herein are copolymers of ethylene preferably having from 0 mol % to 25 mol % (alternately from 0.5 mol % to 20 mol %, alternately from 1 mol % to 15 mol %, preferably from 3 mol % to 10 mol %) of one or more $C_3$ to $C_{40}$ olefin comonomer (alternately from 1 mol % to 15 mol %, preferably from 3 mol % to 10 mol %).

In a preferred embodiment of the invention, the process described herein produces ethylene copolymers comprising from 1 mol % to 99 mol % (preferably 50 mol % to 98 mol %, preferably 75 mol % to 98 mol %) ethylene and from 99 mol % to 1 mol % (preferably 50 mol % to 2 mol %, preferably 2 mol % to 25 mol %, preferably 2 mol % to 15 mol %, preferably 2 mol % to 10 mol %) conjugated diene.

In a preferred embodiment of the invention, the process described herein produces copolymers comprising from 1 mol % to 99 mol % (preferably 50 mol % to 98 mol %, preferably 75 mol % to 98 mol %) ethylene and from 99 mol % to 1 mol % (preferably 50 mol % to 2 mol %, preferably 2 mol % to 25 mol %, preferably 2 mol % to 15 mol %, preferably 2 mol % to 10 mol %) isoprene.

Likewise, the process of this invention may produce olefin terpolymers. In a preferred embodiment of the invention, the ethylene isoprene copolymers produced herein further comprise from 0 mol % to 25 mol % (alternately from 0.5 mol % to 20 mol %, alternately from 1 mol % to 15 mol %, preferably from 3 mol % to 10 mol %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene).

In alternate embodiment, the process of this invention may produce olefin ethylene isoprene copolymers with 0 mol % termonomer.

Typically, the ethylene-conjugated diene copolymers produced herein have an Mw of 5,000 to 250,000 g/mol (preferably 25,000 to 1,000,000 g/mol, preferably 50,000 to 500,000 g/mol), and/or an Mw/Mn between 1 to 50 (alternately 1.4 to 35, alternately 1.5 to 30).

Typically, the ethylene-alphaolefin copolymers produced herein have an Mw of 5,000 to 250,000 g/mol (preferably 25,000 to 1,000,000 g/mol, preferably 50,000 to 500,000 g/mol), and/or an Mw/Mn between 1 to 50 (alternately 1.4 to 35, alternately 1.5 to 30).

Typically, the ethylene homopolymers produced herein have an Mw of 5,000 to 250,000 g/mol (preferably 25,000 to 1,000,000 g/mol, preferably 50,000 to 500,000 g/mol), and/or an Mw/Mn between 1 to 50 (alternately 1.4 to 35, alternately 1.5 to 30).

In a preferred embodiment of the invention, the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versa).

Unless otherwise indicated, Mw, Mn, and Mw/Mn are determined by using a High Temperature Size Exclusion Chromatograph (Polymer Laboratories), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Vol. 34, No. 19, pp. 6812-6820, (2001), and references therein. Three Polymer Laboratories PLgel 10 μm Mixed-B LS columns are used. The nominal flow rate is 0.5 mL/min, and the nominal injection volume is 300 μL. The various transfer lines, columns, viscometer and differential refractometer (the DRI detector) are contained in an oven maintained at 145° C. Solvent for the experiment is prepared by dissolving 6 grams of butylated hydroxytoluene as an antioxidant in 4 liters of Aldrich reagent grade 1, 2, 4 trichlorobenzene (TCB). The TCB mixture is then filtered through a 0.1 μm Teflon filter. The TCB is then degassed with an online degasser before entering the Size Exclusion Chromatograph. Polymer solutions are prepared by placing dry polymer in a glass container, adding the desired amount of TCB, then heating the mixture at 160° C. with continuous shaking for about 2 hours. All quantities are measured gravimetrically. The TCB densities used to express the polymer concentration in mass/volume units are 1.463 g/ml at room temperature and 1.284 g/ml at 145° C. The injection concentration is from 0.5 to 2.0 mg/ml, with lower concentrations being used for higher molecular weight samples. Prior to running each sample, the DRI detector and the injector are purged. Flow rate in the apparatus is then increased to 0.5 ml/minute, and the DRI is allowed to stabilize for 8 to 9 hours before injecting the first sample. The LS laser is turned on at least 1 to 1.5 hours before running the samples. The concentration, c, at each point in the chromatogram is calculated from the baseline-subtracted DRI signal, $I_{DRI}$, using the following equation:

$$c = K_{DRI} I_{DRI} / (dn/dc)$$

where $K_{DRI}$ is a constant determined by calibrating the DRI, and (dn/dc) is the refractive index increment for the system. The refractive index, n=1.500 for TCB at 145° C. and λ=690 nm. For purposes of this invention and the claims thereto, the (dn/dc) values are measured with DRI. Units on parameters throughout this description of the SEC method are such that concentration is expressed in g/cm$^3$, molecular weight is expressed in g/mole, and intrinsic viscosity is expressed in dL/g.

The LS detector is a Wyatt Technology High Temperature DAWN HELEOS. The molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_2 c.$$

Here, $\Delta R(\theta)$ is the measured excess Rayleigh scattering intensity at scattering angle θ, c is the polymer concentration determined from the DRI analysis, $A_2$ is the second virial coefficient, for purposes of this invention $A_2$=0.0006, (dn/dc) is measured with DRI, $P(\theta)$ is the form factor for a monodisperse random coil, and $K_o$ is the optical constant for the system:

$$K_o = \frac{4\pi^2 n^2 (dn/dc)^2}{\lambda^4 N_A}$$

where $N_A$ is Avogadro's number, and (dn/dc) is the refractive index increment for the system. The refractive index, n=1.500 for TCB at 145° C. and λ=657 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$\eta_s = c[\eta] + 0.3(c[\eta])^2$$

where c is concentration and was determined from the DRI output.

All molecular weights are weight average unless otherwise noted. All molecular weights are reported in g/mol unless otherwise noted.

In a useful embodiment, the ethylene conjugated diene copolymers produced herein have a Tm (as measured by DSC) of 150° C. or less (preferably from 0° C. to 130° C., preferably from 20° C. to 80° C., preferably from 60 to 85° C.).

In a useful embodiment, the ethylene alpha-olefin copolymers produced herein have a Tm (as measured by DSC) of 50° C. or more (preferably from 100° C. to 300° C., preferably from 150° C. to 250° C.).

In a useful embodiment, the ethylene homopolymers produced herein have a Tm (as measured by DSC) of 50° C. or more (preferably from 80° C. to 250° C., preferably from 100° C. to 220° C.).

In an alternate embodiment, the copolymer produced has no Tm as determined by DSC.

In a useful embodiment, the ethylene isoprene copolymers produced herein have 1,4 isoprene isomer present in copolymer at 60% or less of the total of 1,4, 3,4 and 1,2 isoprene isomers present (preferably the 1,4 isoprene isomer present 1% to 50%, alternately 2% to 30%, alternately 5% to 20%), as determined by the $^1$H NMR procedure described below.

In a useful embodiment, the ethylene isoprene copolymers produced herein have a 3,4 and 1,2 isoprene isomers present in copolymer at 40% or more of the total of 1,4, 3,4 and 1,2 isoprene isomers present (preferably 50% to 80%, preferably 70% to 95%), as determined by the $^1$H NMR procedure described below.

1,4 isoprene isomer content, 3,4 isoprene isomer content, and 1,2 isoprene isomer content are determined by $^1$H NMR as follows: polymer composition was determined by $^1$H NMR using a Varian DD2 500 MHz instrument run with a 300 flip angle RF pulse, 120 scans, with a delay of 5 seconds between pulses. The polymer sample was dissolved in heated d2-1,1,2,2-tetrachloroethane and signal collection took place at 120° C. The composition of 1,4-isoprene, 3,4-isoprene, 1,2-isoprene, and ethylene were determined from $^1$H NMR.

| Area | Chemical shift | Intensity of each species |
|------|----------------|---------------------------|
| A | 5.0-5.4 ppm | $I_{1,4}$ |
| B | 4.5-4.9 ppm | $I_{3,4} = (B - 2 * C)/2$ |
| C | 5.8-6.0 ppm | $I_{1,2}$ |
| D | 0-3 ppm | $I_{CH2} = (D - 7 * I_{1,4} - 6 * I_{3,4} - 6 * I_{1,2})/2$ |

Mol % 1,4-isoprene = $I_{1,4} * 100/(I_{1,4} + I_{3,4} + I_{1,2} + I_{CH2})$
Mol % 3,4-isoprene = $I_{3,4} * 100/(I_{1,4} + I_{3,4} + I_{1,2} + I_{CH2})$
Mol % 1,2-isoprene = $I_{1,2} * 100/(I_{1,4} + I_{3,4} + I_{1,2} + I_{CH2})$
Mol % E = $I_{CH2} * 100/(I_{1,4} + I_{3,4} + I_{1,2} + I_{CH2})$ To get the total composition, the amount of ethylene (determined from $^1$H NMR) was used. To get the mol % of the total composition, the area of the mol % isoprene from $^{13}$C was multiplied by the total moles of 1,4 and 3,4 from $^1$H NMR, (example: mole cis*.701=mole cis of total). To calculate wt %, the molecular weights of each species were used.

Blends

In another embodiment, the ethylene polymer produced herein is combined with one or more additional polymers prior to being formed into a film, molded part or other article. Useful additional polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, polyisoprene, polychloroprene, polybutadiene, styrene-butadiene rubber, and/or polyisobutylene.

In a preferred embodiment of the invention, the ethylene polymer is present in the above blends, at from 10 wt % to 99 wt %, based upon the weight of the polymers in the blend, preferably 20 wt % to 95 wt %, even more preferably at least 30 wt % to 90 wt %, even more preferably at least 40 wt % to 90 wt %, even more preferably at least 50 wt % to 90 wt %, even more preferably at least 60 wt % to 90 wt %, even more preferably at least 70 wt % to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; cross-linking agents (such as peroxides) and the like.

Applications

Specifically, any of the foregoing polymers, such as the foregoing polypropylenes or blends thereof, may be used in a variety of end-use applications. Such applications include, for example, mono- or multi-layer blown, extruded, and/or cast films or sheets. These films and sheets may be formed by any number of well known extrusion or coextrusion techniques.

The films and sheets may vary in thickness depending on the intended application; however, films and sheets of a thickness from 1 to 1,000 μm are usually suitable. The film or sheet may comprise a sealing layer, which is typically 0.2 to 50 μm on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment of the invention, one or both of the surface layers are modified by corona treatment.

In a particularly useful embodiment of the invention, the copolymers produced herein may be blended with other elastomers, such as general purpose rubber, e.g., butyl rubber, styrene-butadiene rubber, butadiene rubber, polyisoprene, halogenated butyl rubber, natural rubber, nitrile rubber, neoprene rubber, silicon rubber, polyurethane elastomers, BIMS, and other rubbers useful in making such automotive tire components as treads and sidewalls.

The blends of copolymer produced herein and elastomer may be used in traditional elastomer applications that include low permeability elastic membranes (such as tire innerliners and protective clothing fabrics); closures for pharmaceutical and food containers; hot melt sealants; molded syringe plunger tips; hoses and gaskets, and molded and extruded automotive components requiring low permeability such as, gaskets, hoses or hose covers.

Depending upon the desired applications, the amount of rubber present in the composition may range from 10 wt % to 90 wt % of the total polymer content of the composition and the copolymer may range from 90 wt % to 10 wt %, based upon the weight of the composition. In most applications and particularly where the rubber component or copolymer is dynamically vulcanized, the rubber component will constitute less than 70 wt %, more preferably less than 50 wt %, and most preferably 10 wt % to 40 wt % of the total polymer content of the composition.

The blends of copolymer and elastomer may include plasticizers, curatives and may also include reinforcing and non-reinforcing fillers, antioxidants, stabilizers, rubber processing oil, plasticizers, extender oils, lubricants, antiblocking agents, anti-static agents, waxes, foaming agents, pigments, flame retardants and other processing aids known in the rubber compounding art. Such additives can comprise up to 50 wt % of the total composition. Fillers and extenders which can be utilized include conventional inorganics such as calcium carbonate, clays, silica, talc, titanium dioxide, carbon black and the like. The rubber processing oils generally are polybutene, paraffinic, naphthenic or aromatic oils derived from petroleum fractions, but are typically paraffinic oil or polybutenes. The type will be that ordinarily used in conjunction with the specific rubber or rubbers present in the composition, and the quantity based on the total rubber content may range from zero up to 1-200 parts by weight per hundred rubber (phr). Plasticizers such as trimellitate esters may also be present in the composition.

In a useful embodiment, the rubber and/or the copolymer are desirably at least partially crosslinked, and preferably are completely or fully cross-linked. The partial or complete crosslinking can be achieved by adding an appropriate rubber curative to the blend and vulcanizing the rubber to the desired degree under conventional vulcanizing conditions.

Further, if a thermoplastic polymer is also combined with the copolymer or the copolymer and the rubber, it is useful if the rubber and/or copolymer be crosslinked by the process of dynamic vulcanization. The term "dynamic vulcanization" means a vulcanization or curing process wherein the rubber and/or copolymer is vulcanized under conditions of high shear at a temperature above the melting point of the component thermoplastic. The rubber is thus simultaneously crosslinked and dispersed as fine particles within the matrix thermoplastic.

Dynamic vulcanization is effected by contacting or otherwise mixing the thermoplastic elastomer components at elevated temperature in conventional mixing equipment such as roll mills, Banbury mixers, Brabender mixers, continuous mixers, mixing extruders and the like. The unique characteristic of dynamically cured compositions is that, notwithstanding the fact that the rubber component is partially or fully cured, the compositions can be processed and reprocessed by conventional plastic processing techniques such as extrusion, injection molding, blow molding and compression molding. Scrap or flashing can be salvaged and reprocessed.

Those ordinarily skilled in the art will appreciate the appropriate quantities, types of cure systems and vulcanization conditions required to carry out the vulcanization of the copolymer alone or in a blend with a rubber. The material can be vulcanized using varying amounts of curative, varying temperatures and varying time of cure in order to obtain the optimum crosslinking desired. Any known cure system for rubber can be used, so long as it is suitable under the vulcanization conditions with the specific rubber being used and with the thermoplastic component. These curatives include sulfur, sulfur donors, metal oxides, resin systems, peroxide-based systems, hydrosilation curatives, containing platinum or peroxide catalysts, and the like, both with and without accelerators and co-agents. Such cure systems are well known in the art and literature of vulcanization of elastomers. The term "vulcanized" as used in the specification means that the rubber component to be vulcanized has been cured to a state in which the elastomeric properties of the crosslinked rubber are similar to those of the rubber in its conventional vulcanized state, apart from the thermoplastic elastomer composition. The degree of cure can be described in terms of gel content or, conversely, extractable components. Alternatively the degree of cure may be expressed in terms of crosslink density. All of these descriptions are well known in the art, for example in U.S. Pat. Nos. 5,100,947 and 5,157,081.

EXPERIMENTAL

Synthesis of [Cp*ScMe$_2$]$_2$ (Complex 1).

This procedure is adapted from Piers, et al., J. Organomet. Chem., 1991, 407, 51. 1.06 g of [Cp*ScCl$_2$]n was slurried in 60 mL of ether and chilled to −80° C. To this stirring mixture was added 5.4 mL of a 1.64 M solution of methyllithium. The reaction mixture was removed from the cold bath and allowed to warm to room temperature over two hours. Volatiles were stripped from the reaction mixture under vacuum, and 50 mL of toluene and 2 mL of trimethylphosphine were added to the residue. This mixture was stirred vigorously for 45 minutes. The reaction mixture was then filtered through Celite™, and the filtrate was pumped to dryness. The solid so obtained was slurried in hexane and filtered. The solid was dried under vacuum, resulting in 231.5 mg of the desired complex. $^1$H NMR (C$_6$D$_6$, δ): 1.96 (30H), −0.01 (12H).

Supporting Methylalumoxane on Silica

In a nitrogen filled glovebox, 2 kg of toluene and 1 kg of a 30 wt % MAO solution in toluene were added to a reactor and stirred for 5 minutes. To this solution was added 800 g of Davison D 948 600° C. calcined silica. Approximately 100 g of additional toluene was used to wash the silica into the reactor. The reactor was then heated to 100° C. and stirred for 3 hours, followed by an additional 2 hours of stirring while the contents were cooled down to 35° C. The mixture was then placed under vacuum for 5 days, after which the dry silica-supported MAO was unloaded.

Supportation Procedure

In a nitrogen-filled glovebox, 16.8 mg (40 μmol) of bis[pentamethylcyclopentadienyl scandium (III) dimethyl] was dissolved in 1.1 g of toluene and stirred for 10 minutes. This solution was then added to 1.0 g of 600° C. calcined 948 Silica gel onto which 365 mg (6.3 mmol) of MAO had been previously supported. The catalyst solution and the supported MAO were hand stirred together for 10 minutes, and then dried under vacuum overnight. The next morning, 1.01 g of supported catalyst was obtained.

Polymerizations Using [Cp*ScMe$_2$]$_2$

A 2 L steel autoclave reactor was purged with nitrogen for 1 hour at 90° C., and then allowed to cool under nitrogen flow. A mixture of 30 mL of comonomer, 2 mL of a 0.11 M solution of tri-n-octylaluminum in hexane, and 700 mL of isohexane was added to the cooled reactor as a continuous stream via a counter-pressure of nitrogen. Excess nitrogen was subsequently vented off, and the reactor was heated to 80° C. while stirring at approximately 500 rpm. A total of 130 psi of ethylene was then fed into the reactor, with the last 20 psi also used to inject a 2 mL toluene solution containing the catalyst and activator (previously prepared in a glovebox with gentle stirring, in the case of solution runs) or supported catalyst. The reactor was subsequently stirred at 80° C. for 1 hour, with additional ethylene flow controlled via regulator. Afterwards the reactor was cooled, vented to the air, and emptied by hand.

Melt Index Measurements

The clean barrel of a Tinius-Olsen melt index apparatus equipped with a stainless steel orifice measuring 2.095 mm in diameter and 8 mm long was heated to 190° C. Between 3.5 and 4 grams of polyethylene resin was weighed out and then poured into the barrel. The polymer was packed down by hand with a metal plunger, and then a metal piston was placed into the barrel. Three weights totaling 21 kg were placed on the piston, and the assembly was allowed to equilibrate for 6 minutes. The melt index (MI) was then determined for loads of 21.6, 10.0, and 2.16 kg loads using the method described in ASTM 1238D. The data is reported as cc/10 min, and then converted to g/10 min via a set density of 0.7636 g/cc for polyethylene.

Differential Scanning Calorimetry Measurements

DSC measurements were made on a Thermal Analysis Q200. Samples were equilibrated at 25° C., and then heated to 220° C. at 10° C./min. They were then equilibrated at 220° C. and held at this temperature for 3 minutes. The samples were then cooled to −100° C. at 10° C./min, equilibrated at this temperature, before being ramped back to 220° C. at 10° C./min. Heat flow measurements were made every 0.5 sec, and melting temperatures reported here are the second melt.

Gel Permeation Chromatography

Gel permeation chromatography was performed on a Waters Alliance GPC 2000 or a PL GPC 220 (Agilent Technologies) equipped with a differential refractive index (DRI) detector. The solvent consisted of 1,2,4-trichlorobenzene (Sigma Aldrich, Chromasolv grade≥99% purity) stabilized with 1000 ppm of 2,6-di-tert-butyl-4-methylphenol (Sigma Aldrich) and was filtered using a membrane filter (Millipore, polytetrafluoroethylene, 0.1 μm). All samples were dissolved at a concentration of approximately 0.5 to 1.5 mg/mL in this solvent. Dissolution was carried out at 160° C. in a shaker oven for 2-3 hours. The samples were immediately transferred to a sample carousel maintained at 145° C. (Waters Alliance GPC 2000) or an auto-sampler maintained at 150° C.-160° C. (PL GPC 200). Separation was effected by three Mixed B columns in series (Agilent Technologies, PL-Gel 10 μm 300 mm×7.5 mm) at 145° C. (Waters Alliance GPC 2000) or 160° C. (PL GPC 200). The solvent was passed through an in-line filter (Optimize Technologies, SS frit, 2 am) prior to entering the columns at a fixed flow rate of 1.0 mL/min.

Molecular weight was determined by a conventional calibration as described below using a set of seventeen narrow polystyrene standards (Agilent Technologies) with peak molecular weights (Mp) from ~1000 to ~10,000,000 g/mol and Mw/Mn≤1.10. Mp for the polystyrene standard provided on the certificate of analysis from the manufacturer acquired through independent characterization by viscometry and light scattering was used for calibration. The conventional calibration curve was generated by fitting a second order polynomial to a plot of the log Mp vs. retention volume for the polystyrene standards in Microsoft Excel (Version 14.0.7113.5000). Using this calibration and the Mark-Houwink expression, molecular weight moments were determined for polyolefins of known composition. The composition used for GPC analysis was determined by $^{13}C$ NMR or $^1H$ NMR or FTIR.

Determination of Hexene Content by $^1H$ NMR

The $^1H$ solution NMR was performed at a field of at least 500 MHz in tetrachloroethane-d2 solvent at 120° C. with a flip angle of 30°, 5 s delay and 120 transients. Signals were integrated and the numbers of methyl groups per 1000 carbons were reported. The spectrum was referenced to the PE backbone at 1.34 ppm. Methyl groups per 1000 carbons was calculated by taking the Methyl region (0.85-1.05 ppm) and the aliphatic region (0-2.1 ppm).

(Methyl/3)*1000/(aliphatic/2) gives branches per 1000 carbons.

Table 1 below contains solution polymerization data for the copolymerization of ethylene and isoprene with Complex 1. Table 2 contains supported polymerization data for the copolymerization of ethylene and isoprene with Complex 1. Table 3 contains characterization data for selected runs. Table 4 contains solution polymerization data for the copolymerization of ethylene with hexene using Complex 1.

Abbreviations in the tables include: MAO is methylaluminoxane; trityl is trityl tetrakis(pentafluorophenyl)borate; and DMAH is N,N-dimethylanilinium tetrakis (pentafluorophenyl)borate).

TABLE 1

Ethylene/isoprene solution copolymerizations with Complex 1

| Example | Catalyst (µmol) | Activator | Activator (µmol) | Co-monomer | Co-monomer (mL) | Yield (g) | Activity (g/mmol) |
|---|---|---|---|---|---|---|---|
| 1 | 5.71 | MAO | 737.70 | Isoprene | 30 | 0.4856 | 85.1 |
| 2 | 6.90 | Trityl | 6.40 | Isoprene | 30 | 2.604 | 378 |
| 3 | 7.13 | Trityl | 13.01 | Isoprene | 30 | 2.4638 | 345 |
| 4 | 4.04 | Trityl | 8.67 | Isoprene | 30 | 1.3698 | 339 |
| 5 | 5.47 | DMAH | 8.36 | Isoprene | 30 | 0.842 | 154 |
| 6 | 6.18 | DMAH | 8.99 | Isoprene | 30 | 0.498 | 80.5 |
| 7 | 3.09 | Trityl | 3.14 | Isoprene | 30 | 0.274 | 88.6 |
| 8 | 6.18 | Trityl | 7.16 | Isoprene | 30 | 2.7311 | 442 |
| 9 | 4.04 | Trityl | 8.13 | Isoprene | 30 | 0.364 | 90.0 |
| 10 | 2.85 | Trityl | 2.82 | Isoprene | 20 | 0.0716 | 25.1 |
| 11 | 2.85 | Trityl | 3.04 | Isoprene | 40 | 0.026 | 9.11 |
| 12 | 2.85 | Trityl | 3.04 | Isoprene | 40 | 0.0132 | 4.63 |
| 13 | 3.57 | Trityl | 3.36 | Isoprene | 25 | 1.193 | 334 |
| 14 | 3.80 | Trityl | 4.34 | Isoprene | 15 | 6.2558 | 1640 |
| 15 | 2.85 | Trityl | 4.34 | Isoprene | 30 | 1.1992 | 420. |
| 16 | 3.33 | Trityl | 3.36 | Isoprene | 20 | 0.4324 | 130. |
| 17 | 2.85 | Trityl | 3.04 | Isoprene | 30 | 0.1364 | 47.8 |
| 18 | 2.62 | Trityl | 3.04 | Isoprene | 30 | 0.7237 | 277 |
| 19 | 3.57 | Trityl | 3.36 | Isoprene | 15 | 1.4122 | 396 |
| 20 | 3.57 | Trityl | 3.90 | Isoprene | 30 | 0.5518 | 155 |
| 21 | 2.62 | Trityl | 3.25 | Isoprene | 30 | 0.0359 | 13.7 |
| 22 | 2.85 | Trityl | 3.25 | Isoprene | 30 | 0.1224 | 42.9 |
| 23 | 3.33 | Trityl | 3.90 | Isoprene | 30 | 0.008 | 2.40 |
| 24 | 4.52 | Trityl | 4.66 | Isoprene | 30 | 0.0232 | 5.13 |
| 25 | 7.13 | Trityl | 7.81 | Isoprene | 30 | 4.0023 | 561 |

TABLE 2

Ethylene/isoprene supported copolymerizations with Complex 1

| Example | Catalyst (mg) | Comonomer | Comonomer (mL) | Yield (g) | Activity (g/g) |
|---|---|---|---|---|---|
| 26 | 50.10 | Isoprene | 30 | 0.7658 | 15.29 |
| 27 | 53.20 | Isoprene | 30 | 1.0008 | 18.81 |
| 28 | 49.00 | Isoprene | 16 | 0.7606 | 15.52 |
| 29 | 50.10 | None | 0 | 1.3076 | 26.10 |

TABLE 3

Characterization Data for Ethylene/Isoprene Copolymers

| Ex | Mw (g/mol) | Mn (g/mol) | Mw/Mn | Primary Tm (° C.) | Secondary Tm (° C.) | Mol % ethylene | Mol % 1,4 isoprene | Mol % 3,4 isoprene |
|---|---|---|---|---|---|---|---|---|
| 2 | 79,459 | 2,556 | 31.09 | 127.4 | 69.3 | 94.2 | 1.6 | 4.2 |
| 3 | 35,292 | 3,663 | 9.63 | 74.8 | 16.3 | 91.5 | 2.2 | 6.2 |
| 4 | 24,970 | 4,308 | 5.80 | 67.8 | 16.5 | 90.0 | 2.9 | 7.2 |
| 5 | 100,563 | 3,692 | 27.24 | * | * | 92.9 | 1.9 | 5.2 |
| 6 | 33,627 | 11,932 | 2.82 | * | * | 92.9 | 2.0 | 5.1 |

TABLE 3-continued

Characterization Data for Ethylene/Isoprene Copolymers

| Ex | Mw (g/mol) | Mn (g/mol) | Mw/Mn | Primary Tm (° C.) | Secondary Tm (° C.) | Mol % ethylene | Mol % 1,4 isoprene | Mol % 3,4 isoprene |
|---|---|---|---|---|---|---|---|---|
| 8  | 55,380  | 4,860  | 11.40 | 127.7 | 64.1 | 90.5 | 2.6 | 6.9 |
| 13 | 22,153  | 4,691  | 4.72  | 74.5  | 16.9 | 91.9 | 0.5 | 6.2 |
| 14 | 30,269  | 10,651 | 2.84  | 101.6 | 17.4 | 97.6 | 0.5 | 1.9 |
| 15 | 201,257 | 83,035 | 2.42  | 68.0  | 16.3 | 92.7 | 2.0 | 5.4 |
| 18 | 44,875  | 4,006  | 11.20 | *     | *    | 92.0 | 2.3 | 5.7 |
| 19 | 29,381  | 4,320  | 6.80  | 96.6  | 17.1 | 96.5 | 0.8 | 2.7 |

* not measured

TABLE 4

Ethylene/hexene copolymerizations with Complex 1

| Ex | Catalyst (µmol) | Activator | Activator (µmol) | Comonomer (mL) | Yield | Activity (g/mmol) | wt % hexene | MI (10 kg) | MI (21.6 kg) |
|---|---|---|---|---|---|---|---|---|---|
| 30 | 4.8  | Trityl | 5.3 | 30 | 28.2 | 5929 | 0.87 | 0.243 | 1.989 |
| 31 | 51*  | MAO    | —   | 30 | 1.5  | 1373 | 0.51 | †     | †     |
| 32 | 4.8  | None   | —   | 30 | 0.7  | 147  | —    | —     | —     |
| 33 | 3.8  | Trityl | 4.2 | 30 | 20.6 | 4330 | .39  | 3.66  | 12.675 |

NOTE:
Example 31 used a supported catalyst
*mg of supported catalyst
† not measured, All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. The term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa.

What is claimed is:

1. A catalyst compound represented by the formula (I):

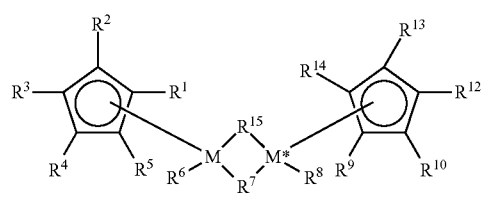

(I)

where M is a group 3 metal;
M* is a group 3 metal;
each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form cyclic fused ring systems;

each $R^7$ and $R^{15}$ is, independently,

—O(R*)— where R* is independently hydrogen, halogen, linear hydrocarbyl, or substituted hydrocarbyl, or -E(R)$_n$—, where E is carbon, silicon, germanium, nitrogen, phosphorus, sulfur, or halogen; n is 0, 1, 2, or 3; each R is independently hydrogen, halogen, hydrocarbyl, or substituted hydrocarbyl; when E is C, Si, or Ge, then n is 2 or 3; when E is N or P, then n is 2; when E is S, then n is 1; and when E is halogen, n is 0; and each $R^6$ and $R^8$ is, independently, a hydrogen, halogen, hydrocarbyl, substituted hydrocarbyl, or silylcarbyl.

2. The catalyst compound of claim 1, wherein M is scandium and M* is scandium.

3. The catalyst compound of claim 1, wherein E is carbon.

4. The catalyst compound of claim 1, wherein each $R^1$, $R^2$, $R^3$, $R^4$, $R^5$, $R^9$, $R^{10}$, $R^{12}$, $R^{13}$, and $R^{14}$ is, independently, hydrogen, methyl, methyl, ethyl, propyl, butyl, pentyl, hexyl, heptyl, octyl, nonyl, decyl, undecyl, dodecyl, $CH_2SiMe_3$, benzyl, $CH_2CMe_3$, $CH(SiMe_3)_2$, $CH_2SiPh_3$, $CH_2CMe_2Ph$ or an isomer thereof; and/or $R^6$ and $R^8$ are independently methyl, ethyl, propyl, butyl, pentyl, hexyl, heptyl, octyl, nonyl, decyl, undecyl, dodecyl, isomers thereof, chloro, iodo, bromo, fluoro, $SiMe_3$, $SiPh_3$, and $CH_2SiMe_3$, $CH_2SiPh_3$, $CH_2SiMe_2Ph$, $CH_2SiMePh_2$, or $CH(SiMe_3)_2$.

5. The catalyst compound of claim 1, wherein the catalyst is represented by the formula (II):

(II)

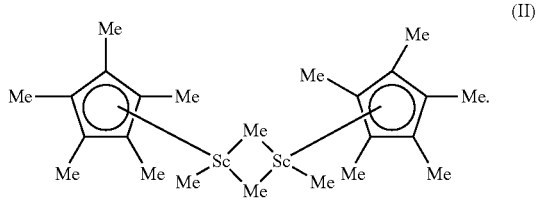

6. The catalyst compound of claim 1, wherein M is scandium or yttrium and M* is scandium or yttrium.

7. The catalyst compound of claim 1, wherein each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form indene or fluorine.

8. A catalyst system comprising an activator and a catalyst compound represented by the formula:

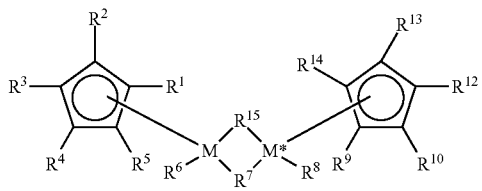

where M is a group 3 metal;
M* is a group 3 metal;
each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form cyclic fused ring systems;
each $R^7$ and $R^{15}$ is, independently, $-E(R)_n-$, where E is carbon, silicon, germanium, nitrogen, phosphorus, oxygen, sulfur, or halogen; n is 0, 1, 2, or 3; each R is independently hydrogen, halogen, hydrocarbyl, or substituted hydrocarbyl; and when E is halogen, n is 0; and
each $R^6$ and $R^8$ is, independently, a hydrogen, halogen, hydrocarbyl, substituted hydrocarbyl, or silylcarbyl.

9. The catalyst system of claim 8, wherein M is scandium and M* is scandium.

10. The catalyst system of claim 8, wherein E is Carbon.

11. The catalyst system of claim 8, wherein each $R^1$, $R^2$, $R^3$, $R^4$, $R^5$, $R^9$, $R^{10}$, $R^{12}$, $R^{13}$, and $R^{14}$ is, independently, hydrogen, methyl, methyl, ethyl, propyl, butyl, pentyl, hexyl, heptyl, octyl, nonyl, decyl, undecyl, dodecyl, $CH_2SiMe_3$, benzyl, $CH_2CMe_3$, $CH(SiMe_3)_2$, $CH_2SiPh_3$, $CH_2CMe_2Ph$ or an isomer thereof; and/or $R^6$ and $R^8$ are independently methyl, ethyl, propyl, butyl, pentyl, hexyl, heptyl, octyl, nonyl, decyl, undecyl, dodecyl, isomers thereof, chloro, iodo, bromo, fluoro, or a silylcarbyl.

12. The catalyst system of claim 8, wherein the catalyst is represented by the formula:

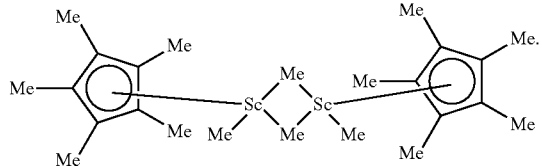

13. The catalyst system of claim 8, wherein the activator comprises alumoxane.

14. The catalyst system of claim 8, wherein the activator comprises a non-coordinating anion activator.

15. The catalyst system of claim 8, wherein the activator is represented by the formula:

$$Z_d^+(A^{d-})$$

wherein Z is (L-H) or a reducible Lewis Acid, L is a neutral Lewis base; H is hydrogen; $(L-H)^+$ is a Bronsted acid; $A^{d-}$ is a non-coordinating anion having the charge d−; and d is an integer from 1 to 3.

16. The catalyst system of claim 8, wherein the activator is represented by the formula:

$$Z_d^+(A^{d-})$$

wherein $A^{d-}$ is a non-coordinating anion having the charge d−; d is an integer from 1 to 3, and Z is a reducible Lewis acid represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl.

17. The catalyst system of claim 8, wherein the activator comprises one or more of:
N,N-dimethylanilinium tetrakis(pentafluorophenyl)borate; triphenylcarbenium tetrakis(pentafluorophenyl) borate; trimethylammonium tetrakis(perfluoronaphthyl)borate; triethylammonium tetrakis (perfluoronaphthyl)borate; tripropylammonium tetrakis(perfluoronaphthyl)borate; tri(n-butyl)ammonium tetrakis(perfluoronaphthyl)borate; tri(t-butyl)ammonium tetrakis(perfluoronaphthyl)borate; N,N-dimethylanilinium tetrakis(perfluoronaphthyl)borate; N,N-diethylanilinium tetrakis(perfluoronaphthyl)borate; N,N-dimethyl-(2,4,6-trimethylanilinium) tetrakis(perfluoronaphthyl)borate; tropillium tetrakis(perfluoronaphthyl)borate; triphenylcarbenium tetrakis(perfluoronaphthyl)borate; triphenylphosphonium tetrakis (perfluoronaphthyl)borate; triethylsilylium tetrakis (perfluoronaphthyl)borate; benzene(diazonium) tetrakis(perfluoronaphthyl)borate; trimethylammonium tetrakis(perfluorobiphenyl)borate; triethylammonium tetrakis(perfluorobiphenyl)borate; tripropylammonium tetrakis(perfluorobiphenyl)borate; tri(n-butyl)ammonium tetrakis(perfluorobiphenyl)borate; tri(t-butyl)ammonium tetrakis(perfluorobiphenyl)borate; N,N-dimethylanilinium tetrakis(perfluorobiphenyl)borate; N,N-diethylanilinium tetrakis(perfluorobiphenyl)borate; N,N-dimethyl-(2,4,6-trimethylanilinium) tetrakis(perfluorobiphenyl)borate; tropillium tetrakis(perfluorobiphenyl)borate; triphenylcarbenium tetrakis(perfluorobiphenyl)borate; triphenylphosphonium tetrakis (perfluorobiphenyl)borate; triethylsilylium tetrakis (perfluorobiphenyl)borate; benzene(diazonium) tetrakis(perfluorobiphenyl)borate; [4-t-butyl-PhNMe$_2$H][(C$_6$F$_3$(C$_6$F$_5$)$_2$)$_4$B]; trimethylammonium tetraphenylborate; triethylammonium tetraphenylborate; tripropylammonium tetraphenylborate; tri(n-butyl)ammonium tetraphenylborate; tri(t-butyl)ammonium tetraphenylborate; N,N-dimethylanilinium tetraphenylborate; N,N-diethylanilinium tetraphenylborate; N,N-dimethyl-(2,4,6-trimethylanilinium) tetraphenylborate; tropillium tetraphenylborate; triphenylcarbenium tetraphenylborate; triphenylphosphonium tetraphenylborate; triethylsilylium tetraphenylborate; benzene(diazonium)tetraphenylborate; trimethylammonium tetrakis(pentafluorophenyl)borate; triethylammonium tetrakis(pentafluorophenyl)borate; tripropylammonium tetrakis(pentafluorophenyl)borate; tri(n-butyl)ammonium tetrakis(pentafluorophenyl)borate; tri(sec-butyl)ammonium tetrakis(pentafluorophenyl)borate; N,N-dimethylanilinium tetrakis(pentafluorophenyl)borate; N,N-diethylanilinium tetrakis(pentafluorophenyl)borate; N,N-dimethyl-(2,4,6-trimethylanilinium) tetrakis(pentafluorophenyl)borate; tropillium tetrakis(pentafluorophenyl)borate; triphenylcarbenium tetrakis(pentafluorophenyl)borate; triphenylphosphonium tetrakis(pentafluorophenyl)borate; triethylsilylium tetrakis(pentafluorophenyl)borate; benzene(diazonium) tetrakis(pentafluorophenyl)borate; trimethylammonium tetrakis-(2,3,4,6-tetrafluorophenyl) borate; triethylammonium tetrakis-(2,3,4,6-tetrafluorophenyl)borate; tripropylammonium tetrakis-(2,3,4,6-tetrafluorophenyl)borate; tri(n-butyl)ammonium tetrakis-(2,3,4,6-tetrafluoro-phenyl)borate; dimethyl(t-butyl)ammonium tetrakis-(2,3,4,6-tetrafluorophenyl) borate; N,N-dimethylanilinium tetrakis-(2,3,4,6-tetrafluorophenyl)borate; N,N-diethylanilinium tetrakis-(2,3,4,6-tetrafluorophenyl)borate; N,N-dimethyl-(2,4,6-trimethylanilinium) tetrakis-(2,3,4,6-tetrafluorophenyl)borate; tropillium tetrakis-(2,3,4,6-tetrafluorophenyl)borate; triphenylcarbenium tetrakis-(2,3,4,6-tetrafluorophenyl)borate; triphenylphosphonium tetrakis-(2,3,4,6-tetrafluorophenyl)borate; triethylsilylium tetrakis-(2,3,4,6-tetrafluorophenyl)borate; benzene(diazonium) tetrakis-(2,3,4,6-tetrafluorophenyl)borate; trimethylammonium tetrakis(3,5-bis(trifluoromethyl)phenyl)borate; triethylammonium tetrakis(3,5-bis(trifluoromethyl)phenyl)borate; tripropylammonium tetrakis(3,5-bis(trifluoromethyl)phenyl)borate; tri(n-butyl)ammonium tetrakis(3,5-bis(trifluoromethyl)phenyl)borate; tri(t-butyl)ammonium tetrakis(3,5-bis(trifluoromethyl)phenyl)borate; N,N-dimethylanilinium tetrakis(3,5-bis(trifluoromethyl)phenyl)borate; N,N-diethylanilinium tetrakis(3,5-bis(trifluoromethyl)phenyl)borate; N,N-dimethyl-(2,4,6-trimethylanilinium) tetrakis(3,5-bis(trifluoromethyl)phenyl)borate; tropillium tetrakis(3,5-bis(trifluoromethyl)phenyl)borate; triphenylcarbenium tetrakis(3,5-bis(trifluoromethyl)phenyl)borate; triphenylphosphonium tetrakis(3,5-bis(trifluoromethyl)phenyl)borate; triethylsilylium tetrakis(3,5-bis(trifluoromethyl)phenyl)borate; benzene(diazonium) tetrakis(3,5-bis(trifluoromethyl)phenyl)borate; di-(i-propyl)ammonium tetrakis(pentafluorophenyl)borate; dicyclohexylammonium tetrakis(pentafluorophenyl)borate; tri(o-tolyl)phosphonium tetrakis(pentafluorophenyl)borate; tri(2,6-dimethylphenyl)phosphonium tetrakis(pentafluorophenyl)borate; triphenylcarbenium tetrakis(perfluorophenyl)borate; 1-(4-(tris(pentafluorophenyl)borate)-2,3,5,6-tetrafluorophenyl)pyrrolidinium; tetrakis(pentafluorophenyl)borate; 4-(tris(pentafluorophenyl)borate)-2,3,5,6-tetrafluoropyridine; and triphenylcarbenium tetrakis(3,5-bis(trifluoromethyl)phenyl)borate).

18. The catalyst system of claim 8 where the catalyst compound and/or the activator are supported.

19. The catalyst system of claim 8, wherein M is scandium or yttrium and M* is scandium or yttrium.

20. The catalyst system of claim 8, wherein each $R^1$, $R^2$, $R^3$, $R^4$, $R^5$, $R^9$, $R^{10}$, $R^{12}$, $R^{13}$, and $R^{14}$ is, independently, hydrogen, a hydrocarbyl, or a substituted hydrocarbyl, where adjacent R groups optionally form indene or fluorine.

21. The catalyst system of claim 8, wherein $R^7$ and $R^{15}$ is, independently, -E(R)$_n$—, where E is carbon, silicon, germanium, nitrogen, phosphorus, oxygen, sulfur, or halogen; n is 0, 1, 2, or 3; each R is independently hydrogen, halogen, hydrocarbyl, or substituted hydrocarbyl; wherein when E is C, Si, or Ge, then n is 2 or 3; when E is N or P, then n is 2; when E is O or S, then n is 1; and when E is halogen, n is 0.

22. The catalyst system of claim 8, wherein each $R^7$ and $R^{15}$ is, independently, -E(R)$_n$—, where E is carbon, silicon, germanium, nitrogen, phosphorus, oxygen, sulfur, fluorine, chlorine, bromine, or iodine; n is 0, 1, 2, or 3; each R is independently hydrogen, halogen, hydrocarbyl, or substituted hydrocarbyl; wherein when -E is C, Si, or Ge, then n is 2 or 3; when E is N or P, then n is 2; when E is O or S, then n is 1; and when E is fluorine, chlorine, bromine, or iodine, n is 0.

23. A process to produce polymers comprising ethylene comprising: 1) contacting ethylene and optional comonomer with the catalyst system of claim 8.

24. The process of claim 23, wherein the polymerization temperature is 60° C. or more.

25. The process of claim 23, wherein comonomer is present.

26. The process of claim 25, wherein the comonomer is conjugated diene.

27. The process of claim 25, wherein the copolymer comprises ethylene and conjugated diene having:
1) from 75 mol % to 99 mol % ethylene;
2) from 1 mol % to 25 mol % conjugated diene;
3) where the mol % amount of the mer unit derived from the conjugated diene where one double bond is incorporated into the copolymer backbone, leaving a pendant double bond, is present at least 1.5 times higher than the mol % amount of the mer unit derived from the conjugated diene where both double bonds are incorporated into the copolymer backbone.

28. The process of claim 25, wherein the copolymer comprises from 75 mol % to 99 mol % ethylene and from 1 mol % to 25 mol % isoprene, where the 3,4 isoprene isomer mol % content in the copolymer is at least 1.5 times higher than the 1,4 isomer mol % content in the copolymer.

29. The process of claim 25, wherein the copolymer comprises 65 mol % to 99.9 mol % ethylene and 0.1 mol % to 35 mol % hexene.

30. The process of claim 23, wherein the process occurs at a temperature of from about 60° C. to about 300° C., at a pressure in the range of from about 0.35 MPa to about 10 MPa, and at a time up to 300 minutes.

31. The process of claim 23, wherein the process occurs in the slurry phase or the gas phase.

32. The process of claim 23, wherein M is scandium and M* is scandium.

33. The process of claim 23, wherein E is carbon.

34. The process of claim 23, wherein each $R^1$, $R^2$, $R^3$, $R^4$, $R^5$, $R^9$, $R^{10}$, $R^{12}$, $R^{13}$, and $R^{14}$ is, independently, hydrogen, methyl, methyl, ethyl, propyl, butyl, pentyl, hexyl, heptyl, octyl, nonyl, decyl, undecyl, dodecyl, $CH_2SiMe_3$, benzyl, $CH_2CMe_3$, $CH(SiMe_3)_2$, $CH_2SiPh_3$, $CH_2CMe_2Ph$ or an isomer thereof; and/or $R^6$ and $R^8$ are independently methyl, ethyl, propyl, butyl, pentyl, hexyl, heptyl, octyl, nonyl, decyl, undecyl, dodecyl, isomers thereof, chloro, iodo, bromo, fluoro, $SiMe_3$, $SiPh_3$, $CH_2SiMe_3$, $CH_2SiPh_3$, $CH_2SiMe_2Ph$, $CH_2SiMePh_2$, or $CH(SiMe_3)_2$.

35. The process of claim 23, wherein the catalyst is represented by the formula (II):

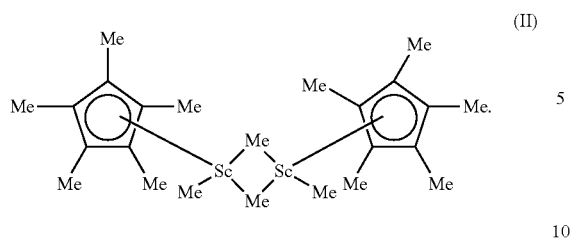

(II)

36. The process of claim 23, wherein the activator comprises alumoxane and/or a non-coordinating anion activator.

37. A process to produce polymers comprising ethylene comprising: 1) contacting ethylene and optional comonomer with the catalyst system of claim 17.

38. A process to produce polymers comprising ethylene comprising: 1) contacting ethylene and optional comonomer with the catalyst system of claim 18.

* * * * *